(12) United States Patent
Ishizuka et al.

(10) Patent No.: US 7,702,374 B2
(45) Date of Patent: Apr. 20, 2010

(54) MEASURING PROBE AND LIVING BODY OPTICAL MEASURING DEVICE

(75) Inventors: Takashi Ishizuka, Ibaraki (JP); Michiyuki Fujiwara, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 1319 days.

(21) Appl. No.: 10/538,236

(22) PCT Filed: Dec. 11, 2003

(86) PCT No.: PCT/JP03/15880

§ 371 (c)(1), (2), (4) Date: Jun. 9, 2005

(87) PCT Pub. No.: WO2004/052211

PCT Pub. Date: Jun. 24, 2004

(65) Prior Publication Data

US 2006/0058594 A1   Mar. 16, 2006

(30) Foreign Application Priority Data

Dec. 12, 2002   (JP) ............................. 2002-360220
Jul. 18, 2003   (JP) ............................. 2003-276767

(51) Int. Cl.
*A61B 5/1455* (2006.01)
(52) U.S. Cl. ...................................... 600/344; 600/340
(58) Field of Classification Search ................. 600/310, 600/315, 316, 319, 322, 323, 326, 328, 340, 600/344
See application file for complete search history.

(56) References Cited

U.S. PATENT DOCUMENTS

| | | | | |
|---|---|---|---|---|
| 4,321,930 A | * | 3/1982 | Jobsis et al. | 600/344 |
| 4,362,360 A | * | 12/1982 | Mannschke | 385/88 |
| 4,510,938 A | * | 4/1985 | Jobsis et al. | 600/344 |
| 4,851,817 A | * | 7/1989 | Brossia et al. | 340/583 |
| 5,786,592 A | * | 7/1998 | Hok | 250/227.14 |
| 5,842,982 A | * | 12/1998 | Mannheimer | 600/340 |
| 6,839,583 B1 | * | 1/2005 | Lewandowski et al. | 600/344 |
| 6,904,302 B2 | * | 6/2005 | Hirabayashi et al. | 600/344 |
| 7,130,672 B2 | * | 10/2006 | Pewzner et al. | 600/324 |

FOREIGN PATENT DOCUMENTS

| | | |
|---|---|---|
| JP | 10-85204 | 4/1998 |
| JP | 11-4830 | 1/1999 |
| JP | 2002-291751 | 10/2002 |
| JP | 2002-355246 | 12/2002 |
| WO | WO 00/74562 | 2/2000 |
| WO | WO00/57793 | 10/2000 |
| WO | WO 00/74562 A1 | 12/2000 |

OTHER PUBLICATIONS

Japanese communication dated Jun. 15, 2009; 2003-276767.

* cited by examiner

*Primary Examiner*—Eric F Winakur
(74) *Attorney, Agent, or Firm*—Antonelli, Terry, Stout & Kraus, LLP.

(57) ABSTRACT

In a measuring probe, the distal ends of an irradiation optical fiber and a detection optical fiber on the subject side are held by a holder portion which is to be mounted on a subject. The optical fibers are led out from the side surface of the holder portion. Further, the optical fibers are bent in the holder portion so that the distal ends of the optical fibers are directed towards the subject when the holder portion is mounted on the subject.

18 Claims, 8 Drawing Sheets

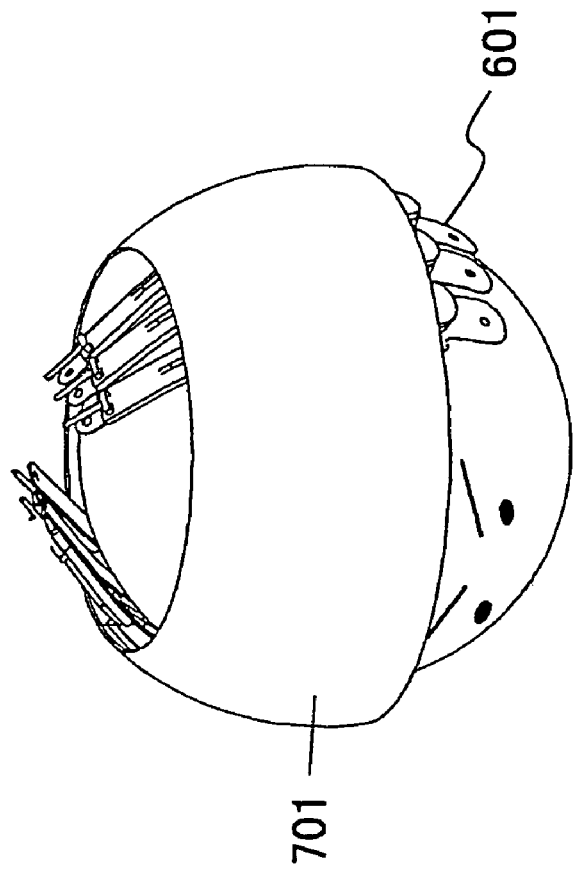
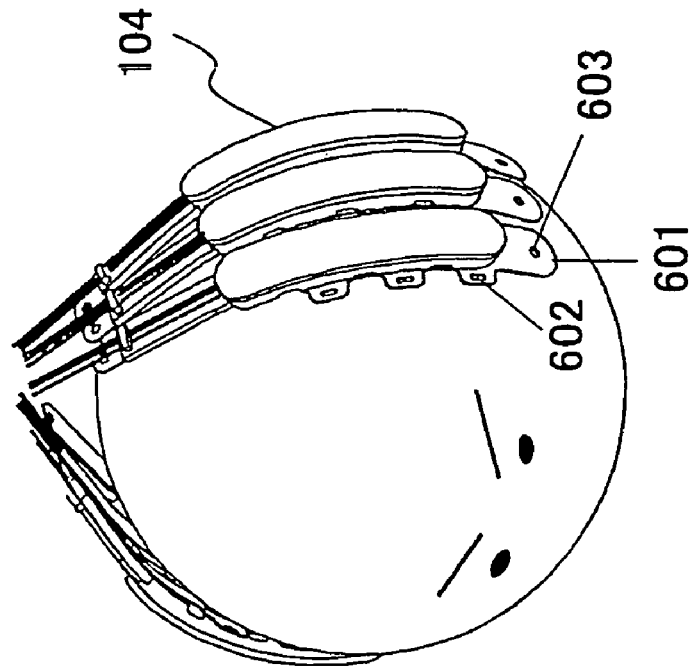

MEASURING PROBE AND LIVING BODY OPTICAL MEASURING DEVICE

TECHNICAL FIELD

The present invention relates to a measuring probe adapted to irradiate a subject with measurement light and receive light transmitted through the subject (living body passing light), and to a living body optical measuring device having the measuring probe.

BACKGROUND ART

As disclosed, for example, in JP 9-98972 A, a conventional living body optical measuring device has a measuring probe attached to a subject and a device main body connected to the measuring probe. The measuring probe has an irradiation optical fiber for irradiating the subject with measurement light generated in the device main body, a detection optical fiber for receiving the measurement light transmitted through the subject, that is, a living body passing light, and guiding it to the device main body; a fixing member for securing the distal end portions of the irradiation and detection optical fibers at predetermined positions of the subject; and a fixation belt for securing the fixing member to the subject.

However, in the case, for example, of the measurement of a newborn baby or a measurement of long duration, it is necessary to perform, apart from a measurement in a seated position or a standing position, measurement in which the subject lies down, and there is demand for a measuring probe allowing such measurement. That is, there is demand for a measuring probe which can be attached to the subject without damaging the optical fibers even when the subject lies down.

DISCLOSURE OF THE INVENTION

The present invention has been made with a view toward solving the above problem. It is accordingly an object of the present invention to provide a measuring probe and a living body optical measuring device which allow measurement with a subject lied down.

To this end, according to one aspect of the present invention, there is provided a measuring probe comprising: a holder portion attached to a subject; and an optical fiber for at least one of irradiation and detection whose distal end portion on a subject side is retained by the holder portion, wherein the optical fiber is led out from a side surface of the holder portion and is bent inside the holder portion such that the distal end portion is directed to the subject when the holder portion is attached to the subject.

According to another aspect of the present invention, there is provided a living body optical measuring device comprising a measuring probe having a plurality of optical fibers that irradiate a subject with measurement light and receive the measurement light returning from the subject, the measuring probe being attached to the subject, wherein the optical fibers are led out from a side surface of the measuring probe and are bent inside the measuring probe portion such that their distal end portions are directed towards the subject when the measuring probe is attached to the subject.

BRIEF DESCRIPTION OF THE DRAWINGS

FIG. 14 is a perspective view of the holder portion of FIG. 11 as attached to a subject;

FIG. 15 is a perspective view of the holder portion of FIG. 14 with a fastening fixing member attached thereto from above;

BEST MODE FOR CARRYING OUT THE INVENTION

In the following, preferred embodiments of the present invention will be described with reference to the drawings.

Embodiment 1

Figure 1:
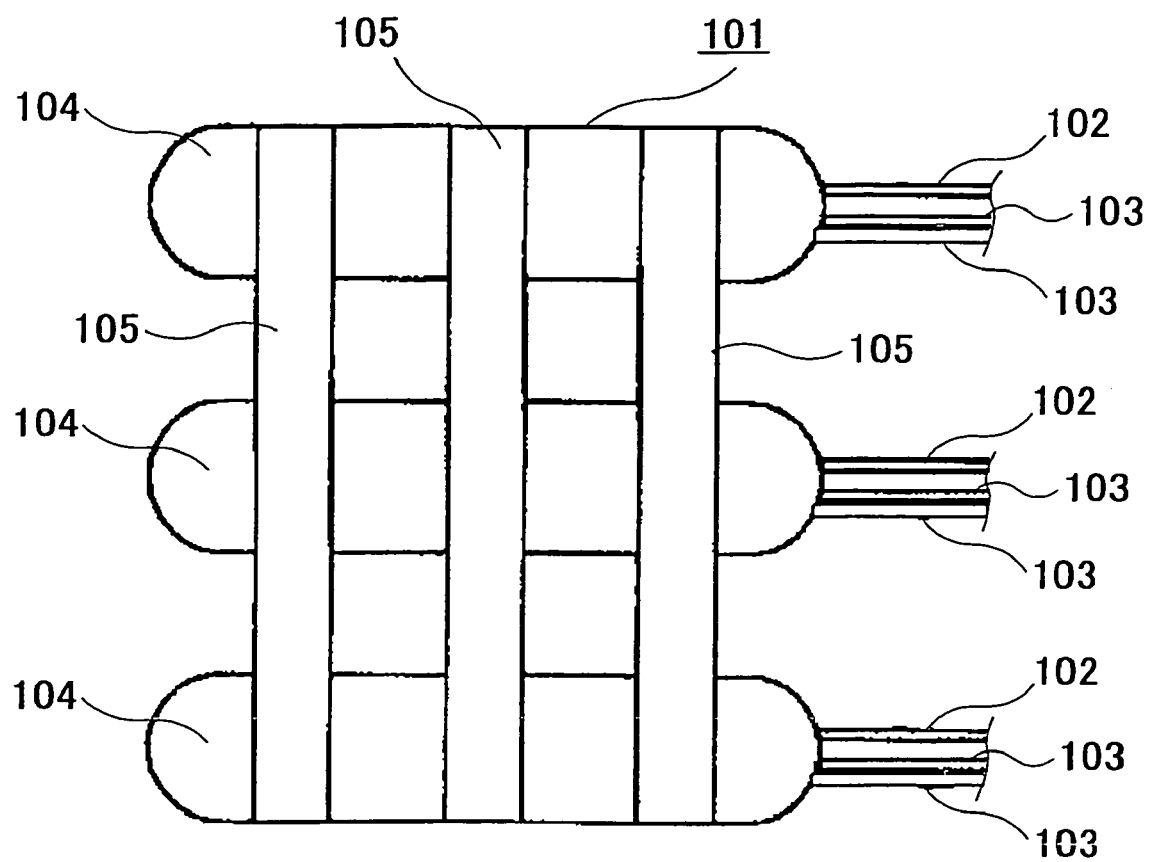
FIG. 1 is a plan view of a measuring probe according to Embodiment 1 of the present invention.

FIG. 1 is a plan view of a measuring probe according to Embodiment 1 of the present invention. In the drawing, the measuring probe of this embodiment has a probe main body 101 to be attached to a subject, a plurality of irradiation optical fibers 102 for guiding irradiation light from the main body of a measuring device to the probe main body 101, and a plurality of detection optical fibers 103 for guiding living body passing light from the subject to the main body of the measuring device.

Unlike the conventional measuring probes, the measuring probe of this embodiment has the irradiation and detection optical fibers 102 and 103 attached in advance to the probe main body 101. Thus, by attaching the probe main body 101 to the subject, the irradiation and detection optical fibers 102 and 103 are respectively arranged at desired measurement positions. That is, by placing the probe main body 101 on the head of the subject, the irradiation and detection optical fibers 102 and 103 are respectively arranged at desired measurement positions.

One end (distal end) of each of the irradiation and detection optical fibers 102 and 103 is retained perpendicular to the surface of the subject with which the probe main body 101 is brought into contact. Also, the irradiation and detection optical fibers 102 and 103 are drawn out of a side surface of the probe main body 101. The other end of each of the irradiation and detection optical fibers 102 and 103 is connected to the measuring device main body.

The probe main body 101 has three holder portions 104. In each holder portion 104, three optical fiber head portions (including an irradiation bed portion and a detection bed portion) are provided at equal intervals. The holder portions 104 are connected together at predetermined intervals by connecting portions 105. As a result, the intervals between the holder portions 104 are maintained, and the measuring probe as a whole is reduced in weight and thickness.

Further, in order that the attachment position of the measuring probe is not shifted even if the subject moves in a horizontal position, such as a prone position, a fixing means (not shown), such as a belt, for securing the measuring probe to the head may be connected to the probe main body 101.

Figure 2:
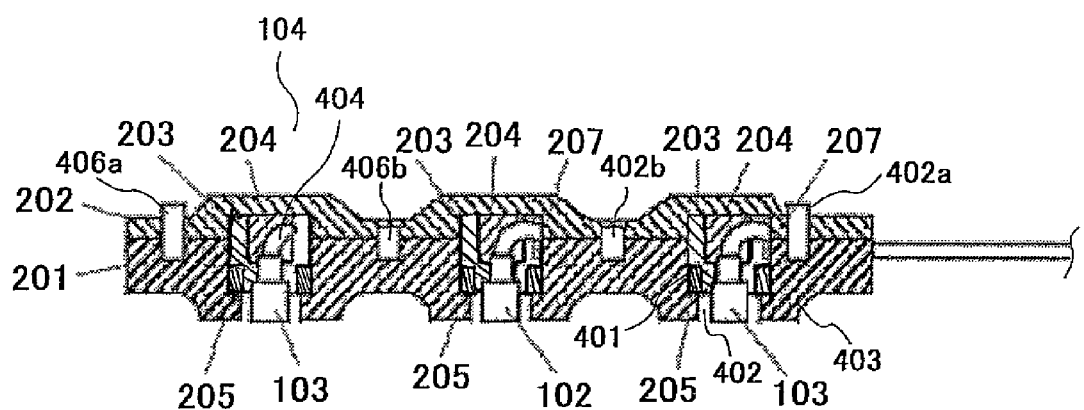
FIG. 2 is sectional view of a holder portion of FIG. 1.
Figure 3:
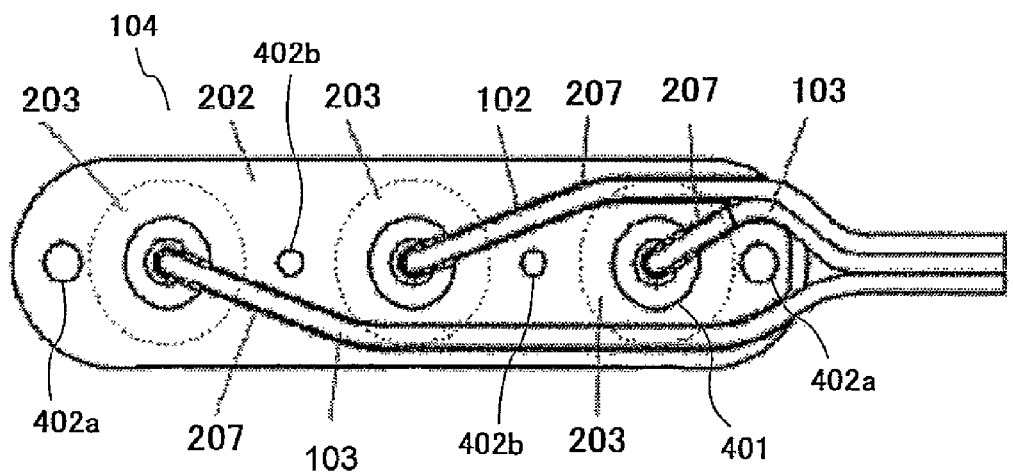
FIG. 3 is a plan view of FIG. 2 with a holder cover removed.
Figure 4:
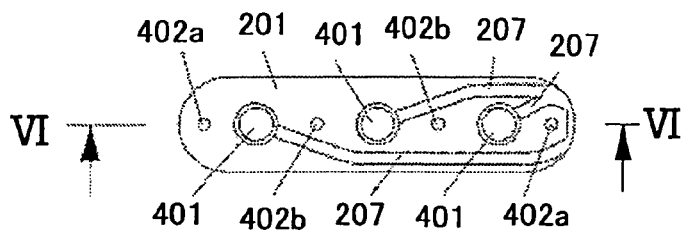
FIG. 4 is a plan view of a holder base of FIG. 2.
Figure 5:
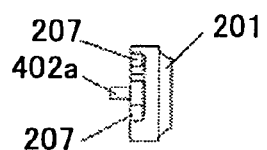
FIG. 5 is a side view of the holder base of FIG. 4.
Figure 6:
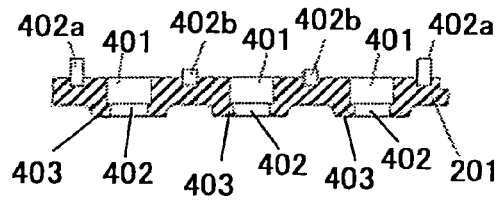
FIG. 6 is a sectional view taken along the line VI-VI of FIG. 4.
Figure 7:
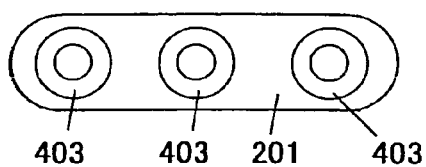
FIG. 7 is a bottom view of the holder base of FIG. 4.
Figure 8:
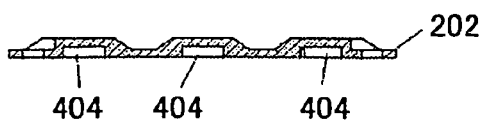
FIG. 8 is a sectional view of the holder cover of FIG. 2.
Figure 9:
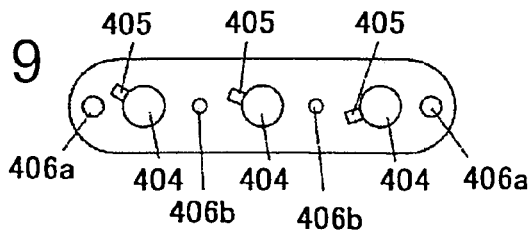
FIG. 9 is a bottom view of the holder cover of FIG. 7.

Next, FIG. 2 is a sectional view of the holder portion 104 of FIG. 1, FIG. 3 is a plan view of FIG. 2 with a holder cover removed, FIG. 4 is a plan view of a holder base shown in FIG. 2, FIG. 5 is a side view of the holder base of FIG. 4, FIG. 6 is a sectional view taken along the line VI-VI of FIG. 4, FIG. 7 is a bottom view of the holder base of FIG. 4, FIG. 8 is a sectional cover of the holder cover of FIG. 2, and FIG. 9 is a bottom view of the holder cover of FIG. 7.

In the drawings, placed on a holder base 201 constituting a first member is a holder cover 202 constituting a second member. The holder base 201 is arranged on the side to be brought into contact with the subject, and the holder cover 202 is arranged on the side not to be brought into contact with the subject. The holder base 201 is formed of a material more flexible than that of the holder cover 202. The holder cover 202 is formed of a material more rigid than that of the holder base 201.

Between the holder base 201 and the holder cover 202, there are retained three optical fibers 102 and 103. A plurality of mutually independent optical fiber arranging grooves (protecting grooves) 207 in which the optical fibers 102 and 103 are accommodated are provided in the holder base 201. Further, the optical fibers 102 and 103 are introduced into the holder portion 104 through a side surface of the holder portion 104, and extend within the holder portion 104 in the direction in which the holder portion 104 extends, with their distal end portions being bent substantially at right angles.

Inside the holder portion 104, there are provided a plurality of optical fiber fixing members 203 for securing the distal ends of the optical fibers 102 and 103, a plurality of optical fiber protecting members 204 for protecting the bent portions of the optical fibers 102 and 103, and a plurality of height adjustment jigs 205 for adjusting the amount by which the optical fibers 102 and 103 protrude from the holder base 201.

The optical fiber fixing members 203 retain the optical fibers 102 and 103 such that the distal end portions of the optical fibers 102 and 103 are arranged at the measurement positions of the subject. Further, the optical fiber fixing members 203 have built-in spring mechanisms (not shown) which retain the optical fibers 102 and 103 and extrude them by a minute amount from the surface of the holder base 201.

The optical fibers 102 and 103 are arranged so as to avoid the optical fiber fixing members 203 for the other optical fibers 102 and 103. For example, the optical fiber 103 arranged at a position nearest to the introducing portion for the optical fibers 102 and 103 passes a side near a first protrusion 402a (described below) for fixing together the holder base 201 and the holder cover 202, and is bent vertically by the optical fiber protecting member 204 before being retained by the optical fiber fixing member 203. The optical fiber 102 arranged at the intermediate position passes the outer side of the optical fiber 103 closest to the introducing portion, and, after being vertically bent by the optical fiber protecting member 204, is retained by the optical fiber fixing member 203. Further, the optical fiber 103 arranged at the position farthest from the introducing portion of the above optical fibers 102 and 103 passes the side opposite to the above-mentioned two optical fibers 102 and 103 with respect to the first protrusion 402a, and is bent vertically by the optical fiber protecting member 204 before being retained by the optical fiber fixing member 203.

The above arrangement of the optical fibers 102 and 103 are effected by inserting the optical fibers 102 and 103 into the optical fiber arrangement grooves 207. In this process, in order to make the bending rate when bending the optical fibers 102 and 103 while protecting them by means of the optical fiber protecting members 204 as low as possible, the outer peripheral coatings of the optical fibers 102 and 103 are removed, and the core portions of the optical fibers 102 and 103 are arranged in the optical fiber arrangement grooves 207.

In the mating surface of the holder base 201 (the surface mated with the holder cover 202), there are provided three recesses 401 with a circular section. At the bottom of each recess 401, there is provided a through-hole 402 leading to the subject side. The distal end portions of the optical fibers 102 and 103 are protruded slightly out of the holder base 201 through the through-holes 402.

The recesses 401 and the through-holes 402 are arranged coaxially. The diameter of the recesses 401 is larger than the diameter of the through-holes 402. As a result, step portions are formed at the bottom of the recesses 401. Further, the diameter of the recesses 401 is the same size as the outer peripheral diameter of the height adjustment jigs 205 and of the optical fiber fixing members 203. The height adjustment jigs 205 and the optical fiber fixation jigs 203 are inserted into the recesses 401.

Further, the holder base 201 has a plurality of annular protrusions 403 protruding so as to surround the distal end portions of the optical fibers 102 and 103 exposed from the holder base 201. By adjusting the amount by which the optical fibers 102 and 103 protrude with respect to the annular protrusions 403 by the height adjustment jigs 205, it is possible to adjust the pressurizing force with which the distal end portions of the optical fibers 102 and 103 abut the subject. Further, due to the annular protrusions 403, external light is prevented from entering the optical fibers 102 and 103 during measurement.

Further, the annular protrusions 403 are formed independently of each other and arranged so as to be spaced apart from each other. As a result, when the measuring probe is arranged on the subject, deformation of the holder portion 104 is allowed such that the annular protrusions 403 are in conformity with the measurement region (abutment region). As a result, it is possible for the optical fibers 102 and 103 to abut the subject at right angles or substantially at right angles. Further, due to the deformation in conformity with the configuration of the measurement region, external light is more reliably prevented from entering the optical fibers 102 and 103 during measurement.

While in this example the external configuration of the annular protrusion 403 formed at the center is circular, and the external configuration of the annular protrusion 403 arranged on either side thereof is elliptical, the configurations of the annular protrusions 403 are not restricted thereto.

The height adjustment jigs 205 prevent excessive burden on the optical fibers 102 and 103 when the moving amount of the optical fibers 102 and 103 at the time of attachment of the measuring probe to the subject exceeds the deformable range of the built-in spring mechanisms of the optical fiber fixing members 203. This helps to prevent the optical fibers 102 and 103 from being damaged.

At the longitudinal ends of the holder base 201, there are formed relatively large first protrusions 402a. Further, between (in the interval) of the recesses 401 adjacent to each other, there are formed second protrusions 402b whose section diameter and protruding amount are smaller than those of the first protrusions 402a.

In the mating surface of the holder cover 202 facing the holder base 201, there are formed a plurality of accommodating portions 404, which are recesses opposed to the recesses 401. The recesses 401 and the accommodating portions 404 define spaces for accommodating the bent portions of the optical fibers 102 and 103. The accommodating portions 404 accommodate the bent portions of the optical fibers 102 and 103, the optical fiber fixing members 203, and the optical fiber protecting members 204. The size of the accommodating portions 404 is set so as to be minimum within the range not involving damage due to the bending of the optical fibers 102 and 103.

Further, the movement of the optical fibers 102 and 103 due to the movement of the distal end portions of the optical fibers 102 and 103 when attaching the measuring probe to the subject is absorbed by the bent portions accommodated in the accommodating portions 404. As a result, the burden on the optical fibers 102 and 103 is substantially reduced, thereby preventing the optical fibers 102 and 103 from being damaged.

Further, the inner peripheral surfaces of the accommodating portions 404 are formed in the same size and configuration as the outer peripheral surfaces of the optical fiber fixing members 203. That is, the accommodating portions 404 also serve as retaining means for retaining the optical fiber fixing members 203. As a result, when the measuring probe is attached to the subject, positional deviation of the optical fiber fixing members 203 is prevented, making it possible to obtain more accurate measurement results.

In order to make the holder cover 202 as thin as possible and to ensure a sufficient strength, protrusions are formed in those portions of the surface thereof on the opposite side of the mating surface (the portion coming into contact with a bed, etc. at the time of measurement) in which the accommodating portions 404 are formed.

In the holder cover 202, there are formed a plurality of grooves 405 through which part of the bent optical fibers 102 and 103 pass. The grooves 405 extend from the accommodating portions 404 in the same direction as the optical fiber arrangement grooves 207. The optical fibers 102 and 103 are partially retained in the grooves 405, whereby the optical fibers 102 and 103 are bent in minimum spaces, and the burden on the optical fibers 102 and 103 is minimized.

Further, in the holder cover 202, there are formed two insertion holes 406a into which the first protrusions 402a are inserted, and two joining recesses 406b into which the second protrusions 402b are fitted. By inserting the first protrusions 402a into the insertion holes 406a and by fitting the second protrusions 402b into the joining recesses 406b, the holder base 201 and the holder cover 202 are combined with each other. Further, the holder cover 202 is fixed to the holder base 201 by screws or the like.

Figure 10:
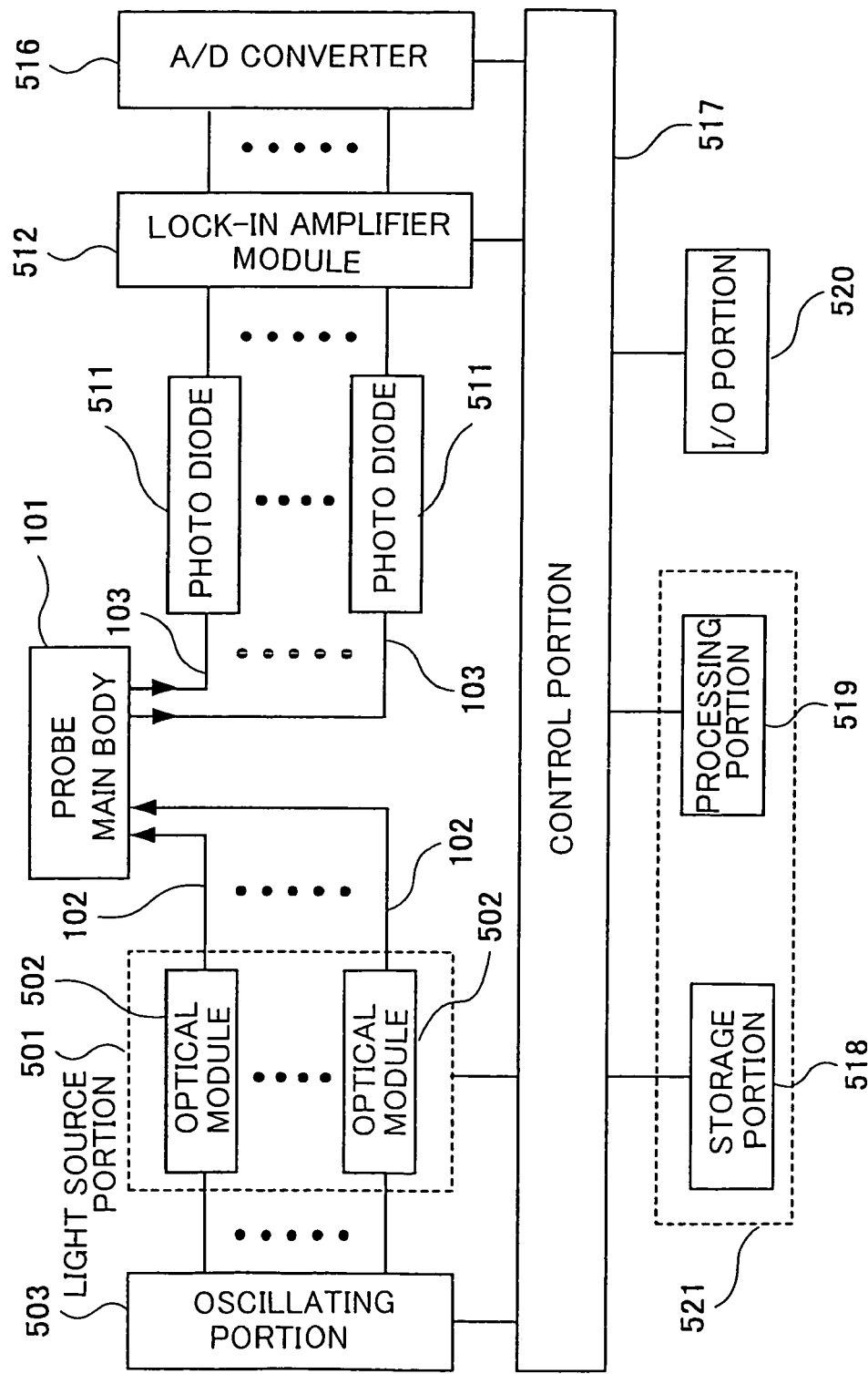
FIG. 10 is a block diagram schematically showing the construction of a living body optical measuring device including the measuring probe of FIG. 1.

Next, FIG. 10 is a block diagram schematically showing the construction of a living body optical measuring device including the measuring probe of FIG. 1. In the drawing, the living body optical measuring device has a probe main body 101, a light source portion 501, an oscillating portion 503, a plurality of photo diodes 511, a lock-in amplifier module 512, an A/D converter 516, a control portion 517, an input/output portion 502, and an image producing portion 521.

The light source portion 501 has a plurality of (for example, four, as in this case) optical modules 502. Each optical module 502 has two semiconductor lasers (not shown) respectively emitting lights of a plurality of wavelengths from the visible to the infrared wavelength region, for example, dual wavelengths of 780 nm and 830 nm.

All the semiconductor lasers included in the light source 501 are modulated by the oscillating portion 503 composed of oscillators of different oscillation frequencies. That is, in the oscillating portion 503, the semiconductor lasers are analog-modulated by a sine wave. Further, each of the optical modules 502 is equipped with an optical fiber connector (not shown) introducing the lights of the wavelengths of 780 nm and 830 nm emitted from the semiconductor lasers into a single irradiation optical fiber 102.

Thus, the light consisting of a mixture of lights of two wavelengths emitted from the light source portion 501 is applied to the subject constituting the object of irradiation from the distal end portions of a plurality of irradiation optical fibers 102 connected to each of the optical modules 502. At this time, the irradiation optical fibers 102 are secured in position at the probe main body 101 as stated above, and apply light to different positions. For example, the distal end portions of the irradiation optical fibers 102 and the detection optical fibers 103 are arranged alternately in a tetragonal-lattice-like fashion inside the probe main body 101.

The living body passing light (the light transmitted through a light scattering reflective body) returning from the subject is detected through a plurality of (for example, five) detection optical fibers 103 arranged in the probe main body 101 by photo diodes (photo detectors) 511 connected to the other ends of the detection optical fibers 103. As the photo diodes 511, it is desirable to adopt well-known avalanche photo diodes which allow high sensitivity optical measurement.

The living body passing light is converted to electric signals (living body passing light intensity signals) by the photo diodes 511. Thereafter, a modulation signal corresponding to the irradiating position and wavelength is selectively detected by a modulation signal selective detection circuit, for example, a lock-in amplifier module 512 composed of a plurality of lock-in amplifiers (not shown).

At this time, the modulation signals output from the lock-in amplifier module 512 are ones respectively separated into living body passing light intensity signals corresponding to the wavelengths and irradiating positions. In the lock-in amplifier module 512, there are used the same number of lock-in amplifiers (not shown) as the number of signals to be measured (for example, 24).

The living body passing light intensity signals analog-output from the lock-in amplifier module 512 are respectively converted to digital signals by an A/D converter (analog/digital converter) 516 of a plurality of (for example, 24) channels. The digital signals are living body passing light intensity signals respectively corresponding to the wavelengths and irradiating positions.

The light source portion 501, the oscillating portion 503, the lock-in amplifier module 512, and the A/D converter 516 are controlled by a control portion 517.

The living body passing light intensity signals converted to digital signals are recorded in a storage portion 518 provided in the image producing portion 521. The living body passing light intensity signals recorded in the storage portion 518 are read at a processing portion 519 which is also provided in the image producing portion 521. In the case of an ordinary living body optical measurement, the processing portion 519 computes changes in oxygenated hemoglobin concentration and changes in de-oxygenated hemoglobin concentration accompanying brain activity, and hemoglobin concentration total amount, based on the living body passing light intensity signals of the detecting positions. The computation results are displayed on a display screen (not shown) of the input/output portion 520 as age-based information on a plurality of measurement positions. The age-based information is stored in the storage portion 518. The method of computation by the processing portion 519 is well known in the art, so a detailed description thereof will be omitted.

In the living body passing light measuring device constructed as described above, the tip portions of the irradiation and detection optical fibers 102 and 103 are introduced into the probe main body 101, and are bent inside the probe main body 101 so as to be perpendicular to the skin of the subject. Thus, even when the subject is in a prone position, it is possible to perform living body optical measurement without damaging the measuring probe (in particular, the irradiation and detection optical fibers 102 and 103).

As a result, it is also possible to perform a living body optical measurement which takes so long as to necessitate the subject to take a rest, such as sleep, which has been difficult in a living body optical measurement using a conventional measuring probe. Thus, it is possible to accurately identify the position of a hypnic epileptic focus or the like, which has conventionally been difficult to identify, making it possible to achieve a substantial improvement in terms of therapeutic performance.

Further, since only the core portions of the optical fibers 102 and 103 are accommodated in the holder portion 104, it is possible to bend the optical fibers 102 and 103 at a smaller radius, making it possible to reduce the thickness of the holder portion 104. As a result, it is possible to further reduce the burden on the subject when performing measurement with the subject lied down.

Further, since the holder base 201 is formed of a material more flexible than that of the holder cover 202, it is possible to further reduce the burden on the subject at the time of attachment.

The number of holder portions 104 is not restricted to three but may be any other number.

Further, the number of optical fibers arranged in one holder portion 104 is not restricted to three, either, but may be any other number.

Further, the routing of the optical fibers 102 and 103 in the holder portion 104 is not restricted to the above-described one.

Furthermore, while in this embodiment the annular protrusions 403 are formed so as to protrude from the holder base 201, this should not be construed restrictively; for example, it is also possible to form the annular recesses 403 by forming recesses extending in the minor axis direction of the holder base 201.

The values of the wavelengths of the lights emitted from the optical modules 502 are not restricted to 780 nm and 830 nm. Further, the number of wavelengths is not restricted to two, either.

Further, while in the above example a semiconductor laser is used as the light source, this should not be construed restrictively; for example, it is also possible to use a light emitting diode.

Furthermore, the method of modulation at the oscillating portion 503 is not restricted to the analog modulation by sine wave; it may also be, for example, a digital modulation using rectangular waves of different time intervals. When thus using digital modulation, a digital filter or a digital signal processor is used as a modulated signal detecting means.

Further, the photo detectors are not restricted to photo diodes; it is also possible to use other photoelectric conversion devices, such as photomultiplier tubes, as long as they are photoelectric conversion devices.

Embodiment 2

Figure 13:
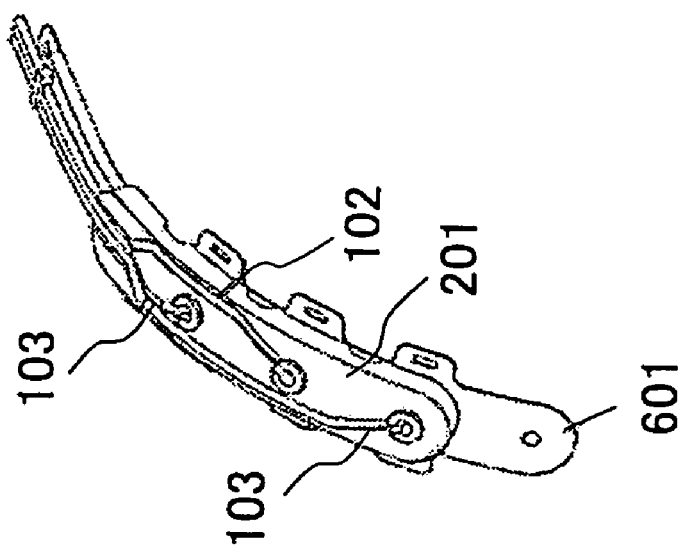
FIG. 13 is a perspective view of the measuring probe of FIG. 11 with the holder cover removed therefrom.
Figure 12:
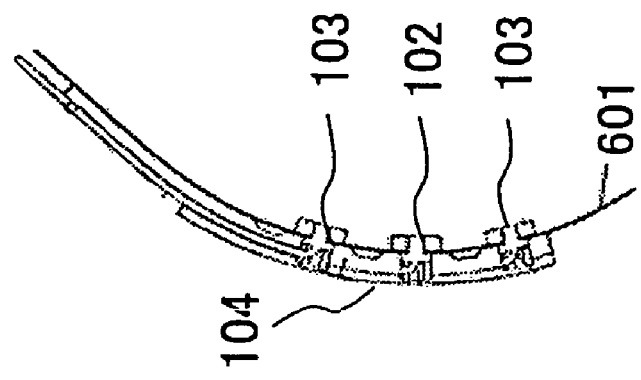
FIG. 12 is a sectional view taken along the line XII-XII of FIG. 11.
Figure 11:
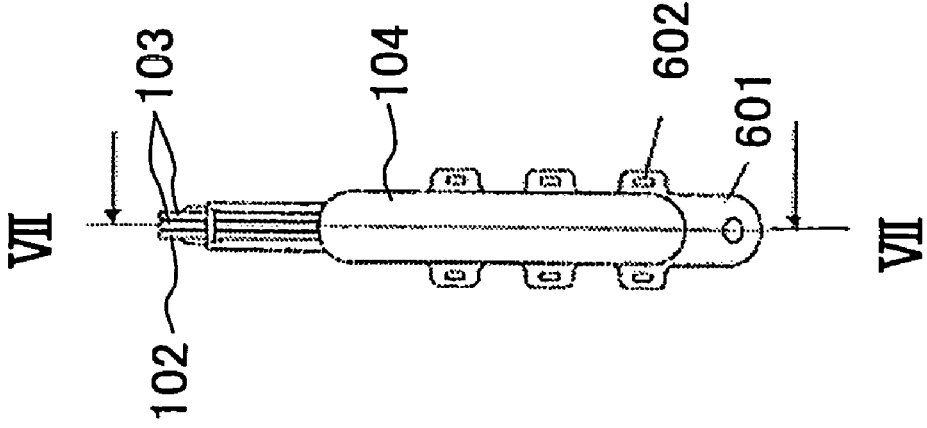
FIG. 11 is a front view of a measuring probe according to Embodiment 2 of the present invention.

Next, FIG. 11 is a front view of a measuring probe according to Embodiment 2 of the present invention, FIG. 12 is a sectional view taken along the line XII-XII of FIG. 11, and FIG. 13 is a perspective view of the measuring probe of FIG. 11 with the holder cover removed therefrom.

In Embodiment 2, in order to match the holder portion 104 with the head configuration of the subject, a base plate 601 as a curving means is bonded to the holder portion 104. The construction of the holder portion 104 is the same as that of Embodiment 1. The base plate 601 is formed of a hard material, such as plastic. Thus, the holder portion 104 is reinforced by the base plate 601.

The base plate 601 is curved in advance. The curvature of the base plate 601 is matched with the head configuration of the subject in advance. The holder portion 104 is maintained in a configuration corresponding to the curved configuration of the base plate 601. Further, the base plate 601 is constructed so as not to interfere with the annular protrusions 403 and the distal end portions of the optical fibers 102 and 103.

By using the base plate 601 described above, it is possible to secure the holder portion 104 in position in a state in which the holder portion 104 is in close contact with the head of the subject. Thus, there is no fear of any undesired gap being generated between the head of the subject and the holder portion 104, making it possible to achieve an improvement in terms of measurement sensitivity.

Further, although not shown, it is also possible to provide rails on the subject side of the holder portion 104, holding the base plate 601 between the rails. This makes it possible to replace the base plate 601 and to combine the relatively soft holder portion 104 with base plates 601 of various configurations, making it possible to modify and attach the holder portion 104 in an optimum manner in conformity with various subject head configurations.

FIG. 14 is a perspective view of the holder portions 104 of FIG. 11 as attached to the subject, and FIG. 15 is a perspective view of the holder portions 104 of FIG. 14 with a fastening fixing member 701 attached from above.

The holder portions 104 are combined with base plates 601 of configurations corresponding to their respective attachment positions. This makes it possible for the holder portions 104 to be fixed in an optimum conformity with the head, which exhibits a fine variation in configuration from position to position.

Further, by attaching the tube-shaped fastening fixing member 701 surrounding the subject, it is possible to prevent the holder portions 104 from being detached, and to hold the holder portions 104 in close contact with the subject. As the material of the fastening fixing member 701, it is possible to use an elastic cloth, a ring-like balloon adapted to expand through injection of air, etc.

The base plates 601 are equipped with connecting portions 602 for the connection of the adjacent base plates 601. The connecting portions 602 may be, for example, of the type in which protrusions and holes are joined with each other or of the type in which attachment is effected by using magnets. This helps to prevent the individual holder portions 104 from being detached.

Further, a connection hole 603 is provided at an end of each base plate 601. It is possible to connect a chin strap or belt (not shown) for the subject to the connection hole 603 as needed.

While in Embodiment 2 the base plate 601 and the holder base 201 are separate from each other, it is also possible to mold the base plate 601 and the holder base 201 integrally with each other.

Further, the base plate may be formed of a material which allows free manual curving and maintenance of the curved state. This makes it possible to perform attachment with the holder portions deformed in an optimum fashion in conformity with various subject head configurations without having to replace the base plates. In this case, the holder portions are formed of a material more flexible than that of the base plates, and are curved in conformity with the curving of the base plates without hindering the maintenance of the curved state of the base plates.

Embodiment 3

Figure 16:
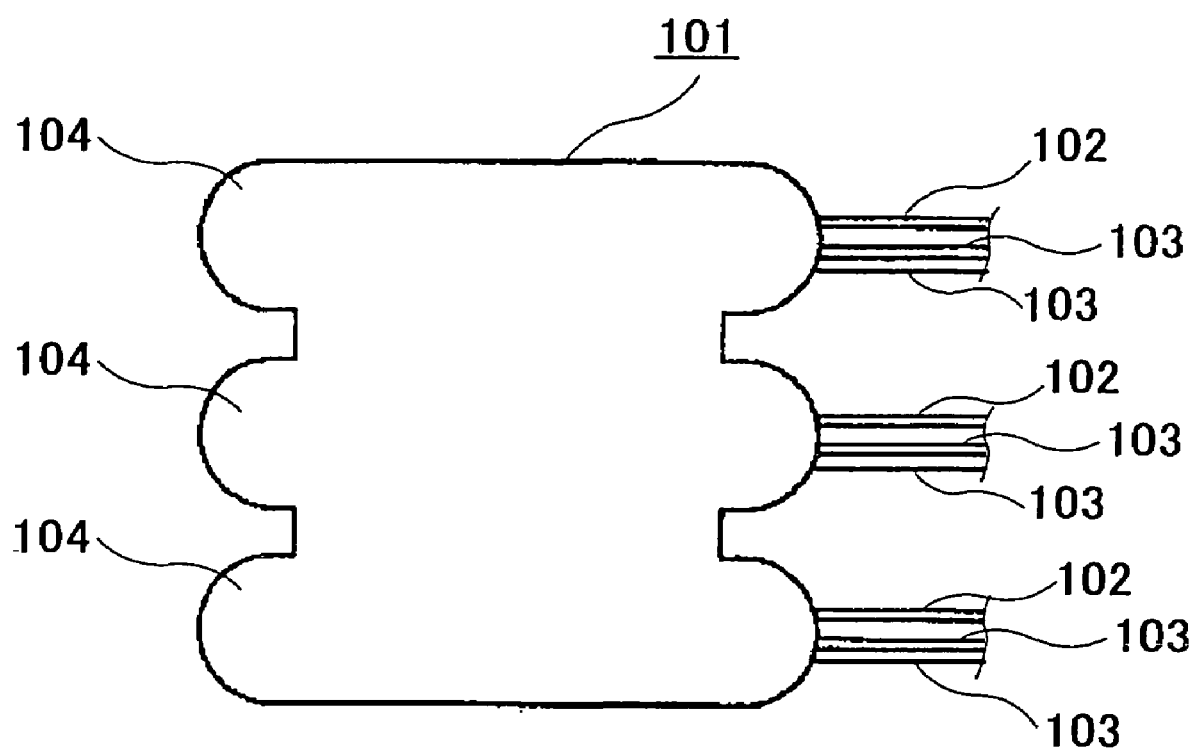
FIG. 16 is a plan view of a measuring probe according to Embodiment 3 of the present invention.

Next, FIG. 16 is a plan view of a measuring probe according to Embodiment 3 of the present invention. While in Embodiment 1 a plurality of holder portions 104 are connected by the connecting portions 105, in Embodiment 3, a plurality of holder portions 104 are previously formed into an integral unit. In this case, at least either the holder bases 201 or the holder covers 202 adopt an integral structure.

Due to this construction, it is possible to achieve a reduction in the number of parts, and to more reliably prevent mutual positional deviation of the holder portions 104.

Embodiment 4

Figure 17:
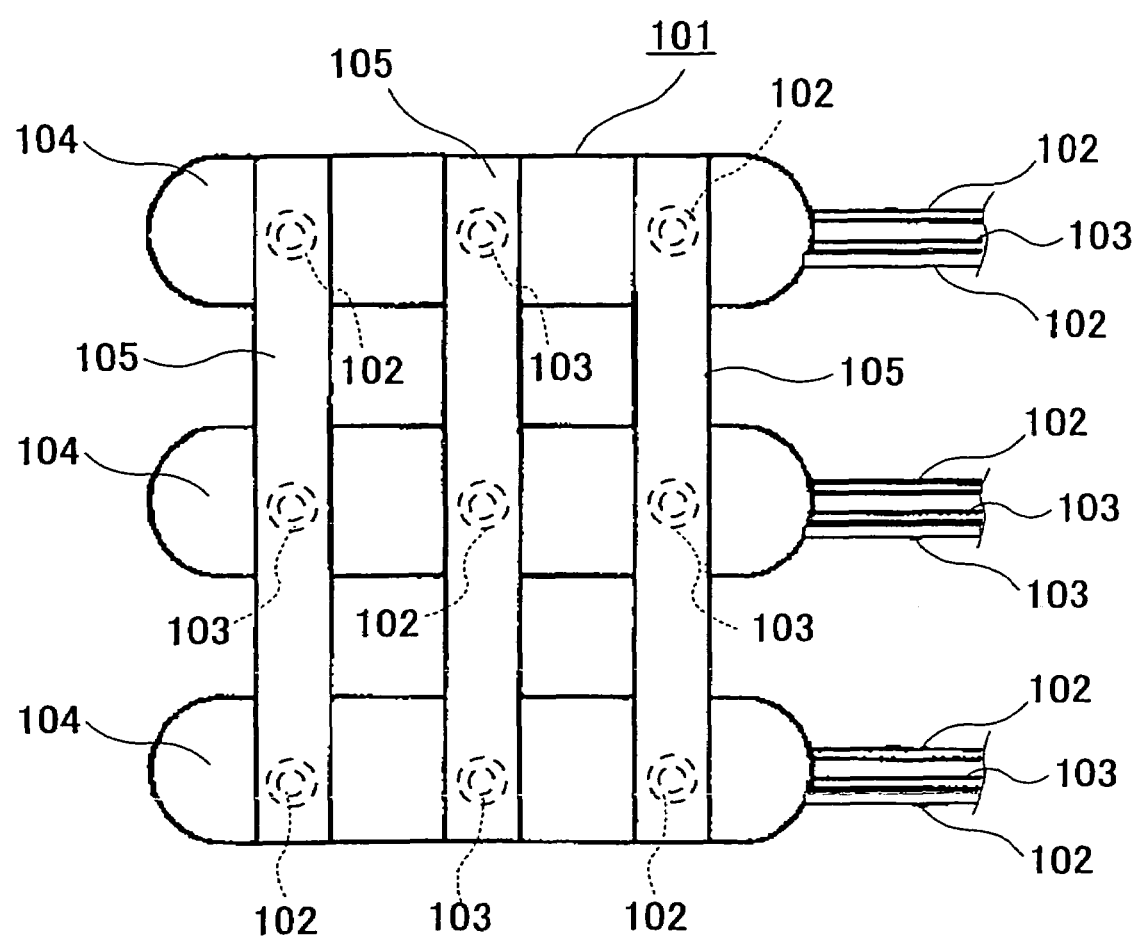
FIG. 17 is a plan view of a measuring probe according to Embodiment 4 of the present invention.

Next, FIG. 17 is a plan view of a measuring probe according to Embodiment 4 of the present invention. In this embodiment, the measuring probe as a whole is formed such that the distal end portions of the irradiation optical fibers 102 and the distal end portions of the detection optical fibers 103 are arranged alternately in both the longitudinal direction of the holder portions 104 (the horizontal direction in FIG. 17) and the direction perpendicular to the longitudinal direction of the holder portions 104. Further, a fixed distance is maintained between the adjacent holder portions 104 by the connecting portions 105.

In the measuring probe described above, the distal end portions of the optical fibers 102 and 103 are arranged in a tetragonal-lattice-like fashion, and the distal end portions of the irradiation optical fibers 102 and the distal end portions of the detection optical fibers 103 are arranged alternately in both of the two directions perpendicular to each other, whereby it is possible to realize a more effective measurement.

The invention claimed is:

1. A measuring probe comprising:
    a holder portion which is adapted to be attached to a subject; and
    an optical fiber for at least one of irradiation and detection, whose distal end portion on a subject side is retained by the holder portion;
    wherein the optical fiber is led out from a side surface of the holder portion and is bent inside the holder portion such that the distal end portion is directed to the subject when the holder portion is attached to the subject;
    wherein an optical fiber fixing member which fixes the distal end portion of the optical fiber is arranged in the holder portion; and
    wherein an optical fiber protecting member which protects the bent portion of the optical fiber is arranged inside the holder portion.

2. A measuring probe according to claim 1, wherein an outer peripheral coating is removed from the bent portion of the optical fiber inside the holder portion.

3. A measuring probe according to claim 1, wherein the holder portion has a first member to be brought into contact with the subject and a second member combined with the first member.

4. A measuring probe according to claim 3, wherein the first member is more flexible than the second member, and wherein the second member is more rigid than the first member.

5. A measuring probe according to claim 3, wherein a protecting groove into which the optical fiber is inserted is formed in at least one of the first member and the second member.

6. A measuring probe according to claim 1, wherein the holder portion is provided with a through-hole through which the distal end portion of the optical fiber is exposed and an annular protrusion protruding so as to surround the distal end portion of the optical fiber.

7. A measuring probe according to claim 1, wherein a space portion for accommodating the bent portion of the optical fiber is provided inside the holder portion.

8. A measuring probe according to claim 7, wherein the holder portion has a first member to be brought into contact with the subject and a second member combined with the first member, and wherein the space portion is formed by combining recesses respectively provided in the first and second members.

9. A measuring probe according to claim 1, wherein a space portion for accommodating the bent portion of the optical fiber and the optical fiber fixing member is provided in the holder portion, and wherein a diameter of the space portion is of the same size as an outer peripheral diameter of the optical fiber fixing member.

10. A measuring probe according to claim 1, wherein a height adjustment jig for adjusting an amount by which the optical fiber protrudes from the holder portion is arranged inside the holder portion.

11. A measuring probe according to claim 1, further comprising a curving means provided on the holder portion, for maintaining the holder portion in a configuration curved along the subject.

12. A measuring probe according to claim 11, wherein the curving means is mounted to the subject side of the holder portion and is a base plate curved in advance.

13. A measuring probe according to claim 11, wherein the curving means is replaceable with respect to the holder portion.

14. A measuring probe according to claim 11, wherein the curving means is provided with a connecting portion for connection with an adjacent curving means.

15. A living body optical measuring device comprising:
    a measuring probe having:
        a plurality of optical fibers that irradiate a subject with measurement light and receive the measurement light returning from the subject, and
        a holder portion which is adapted to attach the measuring probe to the subject;
    wherein the optical fibers are led out from a side surface of the measuring probe and are bent inside the holder portion such that their distal end portions are directed towards the subject when the holder portion attaches the measuring probe to the subject;

wherein an optical fiber fixing member which fixes the distal end portion of the optical fibers is arranged in the holder portion; and wherein an optical fiber protecting member which protects the bent portion of the optical fibers is arranged inside the holder portion.

16. A living body optical measuring device according to claim 15, wherein the measuring probe has a plurality of holder portions, wherein in each of the plurality of holder portions, the distal end portions of the plurality of optical fibers are arranged at intervals.

17. A living body optical measuring device according to claim 15, further comprising a fastening fixing member which is adapted to be put on the subject from above the measuring probe so as to surround the subject and which prevents the measuring probe from being detached from the subject.

18. A measuring probe comprising:

a holder portion which is adapted to attach to a subject; and an optical fiber for at least one of irradiation and detection, the optical fiber having a distal end portion on a subject side which is retained by the holder portion;

wherein the optical fiber is led out from a side surface of the holder portion and is bent inside the holder portion so that the distal end portion is directed to the subject when the holder portion is attached to the subject; and wherein an optical fiber protecting member which protects the bent portion of the optical fiber is arranged inside the holder portion.

* * * * *